(12) United States Patent
Towle (10) Patent No.: US 9,937,218 B2
(45) Date of Patent: Apr. 10, 2018

(54) SYSTEMS AND METHODS FOR CANNABINOID AND TERPENE EXTRACTION AND PURIFICATION

(71) Applicant: Tyrell R. Towle, Mill Creek, WA (US)

(72) Inventor: Tyrell R. Towle, Mill Creek, WA (US)

( * ) Notice: Subject to any disclaimer, the term of this patent is extended or adjusted under 35 U.S.C. 154(b) by 264 days.

(21) Appl. No.: 15/067,970

(22) Filed: Mar. 11, 2016

(65) Prior Publication Data

US 2017/0020944 A1    Jan. 26, 2017

Related U.S. Application Data

(60) Provisional application No. 62/131,781, filed on Mar. 11, 2015.

(51) Int. Cl.
| | | |
|---|---|---|
| *A61K 36/00* | (2006.01) | |
| *A61K 36/185* | (2006.01) | |
| *B01D 11/02* | (2006.01) | |
| *B01D 15/08* | (2006.01) | |
| *B01D 3/14* | (2006.01) | |

(52) U.S. Cl.
CPC ............ *A61K 36/185* (2013.01); *B01D 3/143* (2013.01); *B01D 11/0257* (2013.01); *B01D 11/0288* (2013.01); *B01D 11/0296* (2013.01); *B01D 15/08* (2013.01); *A61K 2236/33* (2013.01); *A61K 2236/37* (2013.01); *A61K 2236/39* (2013.01); *A61K 2236/51* (2013.01); *A61K 2236/53* (2013.01)

(58) Field of Classification Search
CPC ..................................................... A61K 36/00
USPC ............................................................ 424/725
See application file for complete search history.

(56) References Cited

FOREIGN PATENT DOCUMENTS

CN          105816597 A     *    8/2016

* cited by examiner

*Primary Examiner* — Michael V Meller
(74) *Attorney, Agent, or Firm* — Mohr Intellectual Property Law Solutions, P.C.

(57) ABSTRACT

A method for preparing a purified *cannabis* extract may comprise extracting a crude extract from *cannabis* solids, dewatering the crude extract, removing chlorophyll from the crude extract, and distilling the crude extract thereby creating a purified *cannabis* extract. The extracting step may include contacting crude *cannabis* solids with an organic ester, thereby creating the crude extract and waste solids. The dewatering step may include contacting the crude extract with a solid dewatering agent and filtering the crude extract from the solid dewatering agent. The removing chlorophyll step may include contacting the crude extract with a solid absorbent agent, and filtering the crude extract from the solid absorbent agent.

1 Claim, 9 Drawing Sheets

Potency Profile

2.34% CBG-A

<0.01% CBG

2.34% CBG-TOTAL

72.53% Δ9-THC-A 6.05% Δ9-THC

<0.01% Δ8-THC 0.08% CBN

78.66% THC-TOTAL

0.16% CBD-A

<0.01% CBD

0.16% CBD-TOTAL

0.10% CBC

6.23% ACTIVATED-TOTAL

Δ9THC + Δ8THC + CBN + CBD + CBG + CBC

*Cannabinoids that have been activated through decarboxylation (curing/storage of flowers, or heating/cooking of edibles, tinctures, & concentrates)*

Terpene Profile

< 0.01% Linalool

< 0.01% Caryophyllene oxide 2.05% Myrcene

< 0.01% beta-Pinene

< 0.01% Limonene

< 0.01% Terpinolene

< 0.01% alpha-Pinene

< 0.01% Humulene

< 0.01% Caryophyllene 2.05% TERPENE-TOTAL

FIG. 2d

| Category: | Place/ Category | THC Total: | Terpenes Total: | THC + Terpenes | % Unkown |
|---|---|---|---|---|---|
| BHO Shatter Sativa | (1$^{st}$) BSS | 0.55 | 0.16 | 0.71 | 0.29 |
| | (2$^{nd}$) BSS | 0.56 | 0.17 | 0.72 | 0.28 |
| | (3$^{rd}$) BSS | 0.55 | 0.17 | 0.72 | 0.28 |
| BHO Wax Sativa | (1$^{st}$) BWS | 0.60 | 0.10 | 0.70 | 0.30 |
| | (2$^{nd}$) BWS | 0.59 | 0.21 | 0.79 | 0.21 |
| | (3$^{rd}$) BWS | 0.59 | 0.13 | 0.72 | 0.28 |
| CO$_2$ Sativa | (1$^{st}$) CO2 | 0.79 | 0.05 | 0.84 | 0.16 |
| | (2$^{nd}$) CO2 | 0.39 | 0.09 | 0.49 | 0.51 |
| | (3$^{rd}$) CO2 | 0.49 | 0.10 | 0.58 | 0.42 |
| Invention Example 1 | N/A | 0.79 | 0.17 | 0.95 | 0.05 |

FIG. 3

SYSTEMS AND METHODS FOR CANNABINOID AND TERPENE EXTRACTION AND PURIFICATION

CROSS REFERENCE TO RELATED APPLICATIONS

This application claims priority to U.S. Provisional Application Ser. No. 62/131,781, filed on Mar. 11, 2015 which is hereby incorporated by reference for all purposes.

BACKGROUND

The present disclosure relates generally to extraction processes for naturally-occurring compounds. In particular, extraction processes and methods for cannabinoids and terpenes are described.

*Cannabis* is a genus of plants that include three species, *Cannabis sativa*, *Cannabis indica*, and *Cannabis ruderalis*. This genus has long been in use for its hemp fiber material, as milk, seeds and oils, for medicinal purposes, and for recreational use. As more regions approve the use of *cannabis* for both medicinal and recreational use, more *cannabis*-derived products are being produced than ever before. Many of these *cannabis*-derived products utilize the primary psychoactive component of the *Cannabis* plant, tetrahydrocannabinol (THC). *Cannabis* plants initially contain tetrahydrocannabinolic acid (THC-A) and cannabidiolic acid (CBD-A); these compounds break down to THC and cannabindiol (CBD) when exposed to UV light and/or heat. THC belongs to the larger family of cannabinoids. CBD is a non-psychoactive cannabinoid that is used in medicinal preparations. The methods disclosed within this application can be applied to any of these compounds mentioned.

Currently, the primary method for extracting from *Cannabis* plants involves the use of small hydrocarbons such as propane, butane, and hexane. Solvents such as propane, butane, and hexane are highly toxic. Propane is a flammable gas, often used in cooking stoves, and is harmful if its vapors are inhaled or swallowed. Butane is also an organic compound often used in fuel products and refrigerants. Inhalation of butane fumes can cause a range of undesirable effects such as asphyxiation and ventricular fibrillation. Similarly, hexane also causes a host of negative side effects (e.g. nausea, vertigo, intestinal irritation, and CNS effects). Further hazards include more, butane-related explosions and fires when the would-be home chemist attempts to make butane honey oil (BHO).

Butane also has a propensity to extract waxes and other undesired hydrophobic compounds that either remain or require further purification processes to remove from solutions containing cannabinoids. In one embodiment, in order to remove waxes, butane is first allowed to evaporate and the resulting concentrate is re-dissolved in an alcohol-based solution such as isopropyl alcohol or ethanol, and allowed to freeze at −20 degrees Celsius for up to 48 hours to selectively precipitate the waxes out of solution. The resulting mixture then must be vacuum filtered to separate out the precipitated waxes, the alcohol then must be removed from the concentrate through distillation, and finally the mixture purged in a vacuum to reduce the levels of residual solvent to acceptable levels.

Other methods of extracting cannabinoids include the use of FDA "food grade" solvents, such as ethyl alcohol, glycerin, and propylene glycol. While these compounds are safer than the alkanes previously mentioned (e.g. butane, propane and hexane), their properties make it laborious, time-consuming, and difficult to concentrate and purify cannabinoids from the resultant extracts. For instance, water is often a significant portion of ethyl alcohol, some times as much as 60%. The excess of water results in aqueous-soluble impurities such as chlorophyll, flavonoids, and other undesired compounds becoming part of the extract. These impurities can be very challenging to separate from the desired cannabinoid compound. In order to remove these impurities, the unpurified mixture often has to be dissolved in toxic solvents such as chloroform and then subjected to numerous extraction and chromatographic separations. The use of toxic solvents does not give the impression of "clean medicine" or "food grade" compounds. Finally, the use of these existing extraction techniques and purification methods is likely to be unprofitable in a scaled up production due to costs associated with more expensive laboratory equipment and training individuals to perform such tasks safely and without impacting the environment.

In addition to cannabinoids, similar compounds such as terpenes would also benefits from less toxic methods of extraction. Terpenes are resins and volatile compounds found in many kinds of plants including conifers and flowering plants. Terpenes are useful in the food, cosmetic, pharmaceutical and biotechnology industries.

Thus, there exists a need for cannabinoid and/or terpene extraction processes that improve upon and advance the design of known extraction processes. Examples of new and useful cannabinoid and terpene extraction processes relevant to the needs existing in the field are discussed below.

Disclosure addressing one or more of the identified existing needs is provided in the detailed description below. Examples of references relevant to cannabinoid extraction techniques include U.S. Patent References: U.S. Pat. No. 6,403,126 to Webster ("Webster"), U.S. Pat. No. 8,530,679 to Bhatarah ("Bhatarah"), and U.S. Pat. No. 6,365,416 to Elsohly ("Elsohly").

The method described in Webster extracts cannabinoids using organic solvents. These solvents include petroleum-derived hydrocarbons such as toluene and trimethylpentane or alcohol such as ethanol or dicholormethane, a low molecular weight chlorinated hydrocarbon. Toluene, trimethylpentane, and dichloromethane are all toxic and flammable. Furthermore, Webster describes extracting cannabinoid using subcritical water and supercritical fluid such as carbon dioxide. While these latter techniques involve non-harmful compounds, performing extractions with supercritical fluids and subcritical water requires more sophisticated equipment as well as expertise to perform compared to the simple extraction technique described in this application.

The process described in Bhatarah also uses organic solvents for extracting the cannabinoids. The solvents specifically pointed out are n-propane, isopropane, cyclopropane, n-butane, isobutane and isobutylene. As mentioned earlier, butane and its counterparts, are highly flammable and thus dangerous. Furthermore, residual butane left after the extraction process can be harmful to the user. Additionally, butane and like compounds also have the tendency to extract waxes and other undesirable hydrophobic compounds which may need to be removed with additional steps.

The method described in Elsohly also uses organic solvents. The organic solvents mentioned are hexane, heptane or iso-octane. Similar to the solvents mentioned earlier, these compounds are not fit for human consumption and could create adverse effects if ingested. Furthermore, the method described in Elsohly requires both purification using column chromatography and large-scale HPLC. Both of these methods require expensive lab ware and purification systems. Finally, the solvents used in both of the purification steps are also toxic and not fit for human consumption.

DETAILED DESCRIPTION

The disclosed systems and methods for extraction and/or purification of cannabinoids and terpenes will become better understood through review of the following detailed description in conjunction with the figures. The detailed description and figures provide merely examples of the various inventions described herein. Those skilled in the art will understand that the disclosed examples may be varied, modified, and altered without departing from the scope of the inventions described herein. Many variations are contemplated for different applications and design considerations; however, for the sake of brevity, each and every contemplated variation is not individually described in the following detailed description.

Throughout the following detailed description, a variety of cannabinoid and terpene extraction systems and methods are described. Related features in the examples may be identical, similar, or dissimilar in different examples. For the sake of brevity, related features will not be redundantly explained in each example. Instead, the use of related feature names will cue the reader that the feature with a related feature name may be similar to the related feature in an example explained previously. Features specific to a given example will be described in that particular example. The reader should understand that a given feature need not be the same or similar to the specific portrayal of a related feature in any given figure or example.

A method for preparing a purified cannabis extract in accordance with the present disclosure may comprise extracting a crude extract from cannabis solids, dewatering the crude extract, removing chlorophyll from the crude extract, and distilling the crude extract thereby creating a purified cannabis extract. As described below, the extraction process may extract cannabinoids and/or terpenes using relative easy methods and a minimal use of expensive laboratory equipment.

The disclosed process addresses many of the shortcomings existing with conventional extraction methods for cannabinoids and terpenes. For example, the process described uses FDA food-safe, environmentally-friendly, and efficient method for extracting cannabinoids and terpenes. Furthermore, the process provides product yields that are comparable to traditional extraction methods that use more toxic solvents and conditions.

As described above, a method for preparing a purified cannabis extract may comprise extracting a crude extract from cannabis solids. The extracting step comprises contacting crude cannabis solids with an organic ester. The contact between the crude cannabis solids and the organic ester may cause at least some of the cannabinoid and/or terpene compounds to transfer from the crude cannabis solids and into the extraction solvent. Thus, a crude extract and waste solids may be produced.

In some embodiments, the contact between the crude cannabis solids and the organic ester may take place inside a closed system. For example, in some embodiments, the contact may take place in a recirculating extraction vessel. In one embodiment, the recirculating extraction vessel is a soxhlet apparatus. In another example, the recirculating extraction vessel is an APOTHECARIAN apparatus. If a soxhlet is used for the extraction, the crude cannabis solids may be loaded into the thimble of a soxhlet and the organic ester may be loaded into the flask of the soxhlet. The soxhlet may then be configured to reflux the organic ester through the crude cannabis solids.

While a soxhlet or other recirculating extraction vessel may be used as described above, in other embodiments, the extracting step may comprise a simple direct soaking of the crude cannabis solids in the organic ester. Such simple soaking extractions may occur in a closed or an open vessel.

The extracting step may optionally include heating or cooling the organic ester. For example, if a soxhlet is used for the extraction, refluxing the organic ester may require heating of the organic ester.

The extraction step may extract one or more cannabinoid and or terpene compounds from the crude cannabis solids. These compounds may include THC-A, THC, CBD, CBD-A, and/or terpenes. The extraction solvent may comprise one or more food grade, non-toxic solvents. Such solvents may preferably be a liquid at room temperature. In some embodiments, the solvent comprises one or more organic esters. In a preferred embodiment the solvent comprises ethyl acetate (EtOAc). In other embodiments, the solvent may comprises ethyl alcohol and/or propylene glycol. As described above, in some embodiments, ethyl alcohol and/or propylene glycol may result in undesirable effects on the composition of the extract.

The temperature of the extraction solvent during the extraction may be adjusted in order to control the composition of the extract. Thus, the extraction process can be performed at below room temperature, room temperature, or above room temperature. While the extraction process can be performed at below room temperature or at room temperature, the exaction process preferably is performed at above room temperature.

In some embodiments, the temperature of the extraction solvent during extraction is 20 to 100 degrees Celsius. In one embodiment, the temperature of the extraction solvent during extraction is 20 to 80 degrees Celsius. In another embodiment, the temperature of the extraction solvent during extraction is 60 to 80 degrees Celsius. In another embodiment, the temperature of the extraction solvent during extraction is 40 to 90 degrees Celsius. In another embodiment, the temperature of the extraction solvent during extraction is not greater than 0 degrees Celsius. In another embodiment, the temperature of the extraction solvent during extraction is 0 to 20 degrees Celsius.

As described above, in some embodiments, the extraction may take place in a closed vessel. In this regard, the pressure during the extraction may be controlled. In one embodiment, the extraction may occur at pressure above atmospheric pressure. In another embodiment, the extraction may occur at pressure below atmospheric pressure.

The duration of the extraction process may also be controlled in order to control the composition of the extract. For example, in some embodiments, a short duration extraction time is used in order to obtain high quantities of THC and terpene extracts. A short duration extraction may have a duration of not greater than 10 minutes. In some embodiments, a longer duration extraction time can also be used. A long extraction duration can be used to more fully extract other non-terpene phytochemicals and waxes. In some embodiments, a long extraction may have a duration of 10 minutes to 30 minutes. The longer extraction time results in a more traditional "BHO shatter"-like consistency. Often a longer extraction duration results in higher THC concentrations but a lower terpene concentration compared to a shorter extraction duration. In some embodiments, the extraction may have a duration of 5 to 30 minutes. Extraction durations greater 30 minutes may not be desirable because it was found to produce accumulation of waxes and other unwanted constituents.

After the crude extract is obtained, the crude extract may be dewatered. Dewatering the crude extract may comprise contacting the crude extract with a solid dewatering agent. As a result of the contact between the crude extract and the solid dewatering agent, at least some water may transfer from the crude extract and into the dewatering agent.

The dewatering step may further comprise filtering the solid dewatering agent out of the crude extract. Thus, the dewatering step may remove at least a portion of any water present in the crude extract after the extraction step. Filtration of the solid dewatering agent can be performed using, for example, gravity filtration and/or vacuum-assisted filtration, among many others. In one embodiment, Whatman #1 Qualitative filters may be used.

In some embodiments, the solid dewatering agent may be added to the crude extract as solid granules, the solid granules may then be mixed or agitated, and then filtered out of the crude extract. In other embodiments, the dewatering step may be performed via a filtration cartridge. The filtration cartridge may comprise an inlet, an outlet, a chamber housing the solid dewatering agent and a filter. The filtration cartridge may also be used in many other extraction processes to improve the quality of the *cannabis* resin. For example, it may be included in-line in a sub- or supercritical $CO_2$ extractor to remove water, chlorophyll, and other impurities during the process.

In some embodiments, the solid dewatering agent may be a hygroscopic solid which is either approved for use in food by the FDA or pharmaceutical grade. In some embodiments, the solid dewatering agent may comprise one or more of sodium sulfate, magnesium sulfate, and silica.

Additionally or alternatively to dewatering, the chlorophyll may be removed from the crude extract. Removing chlorophyll from the crude extract may comprise contacting the crude extract with a solid absorbing agent. As a result of the contact between the crude extract and the solid absorbing agent, at least some chlorophyll may transfer from the crude extract and into the absorbing agent.

The removing chlorophyll step may further comprise filtering the solid absorbing agent out of the crude extract. Thus, the removing chlorophyll step may remove at least a portion of any chlorophyll present in the crude extract after the extraction step. Filtration of the solid absorbing agent can be performed using, for example, gravity filtration and/or vacuum-assisted filtration, among many others. In one embodiment, Whatman #1 Qualitative filters may be used.

In some embodiments the removing chlorophyll step and the dewatering step may be concomitant. Thus, in some embodiments, the solid absorbing agent and the dewatering agent may be added together to the crude extract as solid granules, the solid granules may then be mixed or agitated, and then filtered out of the crude extract.

In other embodiments, the removing chlorophyll step may be performed via a filtration cartridge. In some embodiments, the filtration cartridge may be a combination dewatering and chlorophyll removal cartridge. Thus, in some embodiments, the chamber of the filter cartridge may house both a solid dewatering agent and a solid absorbing agent. In other embodiments, the chlorophyll and/or water removal cartridge may be a separate stand-alone cartridge.

In some embodiments, the solid dewatering agent may be an absorbent (e.g., porous) solid which is either approved for use in food by the FDA or pharmaceutical grade. In some embodiments, the solid absorbing agent may comprise one or more of Fuller's earth, activated charcoal, and silica.

The method of preparing a purified *cannabis* extract may include winterizing the crude extract. In some embodiments, the winterizing step may include cooling the crude extract in order to precipitate one or more waxes from the crude extract. In some embodiments, the crude extract may be cooled to a temperature of below 0 degrees Celsius. The precipitated wax may then be filtered from the cooled crude extract.

The method of preparing a purified *cannabis* extract may further comprise distilling the crude extract. The distillation step may remove a majority of the extraction solvent, thereby producing the purified *cannabis* extract. Suitable distillation methods include fractional distillation, simple distillation, and vacuum distillation. Using fractional distillation may produce a purified *cannabis* extract containing a higher level of terpenes than with other distillation methods. As described below, in one example, fractional distillation step lead to 78% THC and 16% terpenes. Thus, in some embodiments, the refined *cannabis* extract solid comprises at least 10 wt. % terpenes. In other embodiments, the refined *cannabis* extract solid comprises at least 15 wt. % terpenes. Using simple distillation may produce a purified *cannabis* extract that loses many of the lower boiling terpenes. As described below, in one example after simple distillation, the resulting product contained 70% THC and 2% terpenes.

After distillation, a portion of any remaining residual extraction solvent may be removed via vacuum purging, thereby producing a refined *cannabis* extract solid. Vacuum purging can be done at or above room temperature. In some embodiments, the vacuum purging can be performed in a vacuum chamber, a vacuum oven, or other suitable vacuum set-up.

Example 1—Extraction Protocol Example 30 g freshly dried Dutch Treat variety of *Cannabis sativa* L. was gently broken apart by hand and loaded into Soxhlet extraction thimbles, approximately 4 g per thimble. Fresh EtOAc (200 mL) was added to a 1000 mL boiling flask which was equipped with a Teflon coated stir bar. The Soxhlet apparatus was assembled (with extraction thimble in place) with clamps to sit directly on top of a VWR stirring hot plate. Ice cold water was circulated through the reflux condenser throughout the experiment.

The boiling flask was then heated with vigorous stirring until the EtOAc began boiling and condensing above. The heat was then lowered in order to maintain a constant rate of condensation. Each extraction thimble was allowed to fill and siphon a total of two times per batch of plant matter. Some siphoned early, resulting in only 1.5 siphons.

As soon as the second siphon began, the boiling flask was removed from the heat and allowed to rest until no solvent condensation was evident. The condenser was then separated from the Soxhlet apparatus and the consumed plant matter removed carefully with large tongs. A new extraction thimble was immediately placed into the Soxhlet, the condenser set atop, and returned to heat and vigorous stirring. The extraction thimble was allowed to fill and siphon 2 times before removal of the consumed plant matter. The process was repeated until all of the plant matter was extracted.

Once the last extraction thimble was finished, the boiling flask was removed from the heat source and allowed to cool to room temperature before proceeding. Once cooled, about 5 g food grade sodium sulfate was added to the boiling flask and swirled around until it was evident that the salt crystals flowed smoothly on the bottom of the flask. The solution immediately became clearer upon removal of the water.

After water removal, the EtOAc was decanted into a large beaker. To this beaker was added a few grams of food grade, finely powdered activated charcoal. The beaker was swirled and the activated charcoal was allowed to settle in order to verify color and clarity of the solution before proceeding. At this point, the solution was clear and brilliant yellow.

This solution was then decanted/filtered through a Whatman #1 filter directly into a 500 mL round bottom flask (RBF) already equipped with a Teflon coated stir bar. The RBF was then placed into a hot oil bath on top of the stirring hot plate. The fractional distillation column (equipped with steel wool ["Scrub Buddy" brand steel wool, available from Amway, Seattle, Wash.]) was equipped with a thermometer, and the condenser assembled. The apparatus drained into a 250 mL collection beaker.

The RBF was then heated with vigorous stirring, and the heat lowered once it was evident that distillation had commenced. The temperature was carefully monitored to not go above 80 C in order to ensure adequate retention of the volatile terpenes.

Figure 1A:
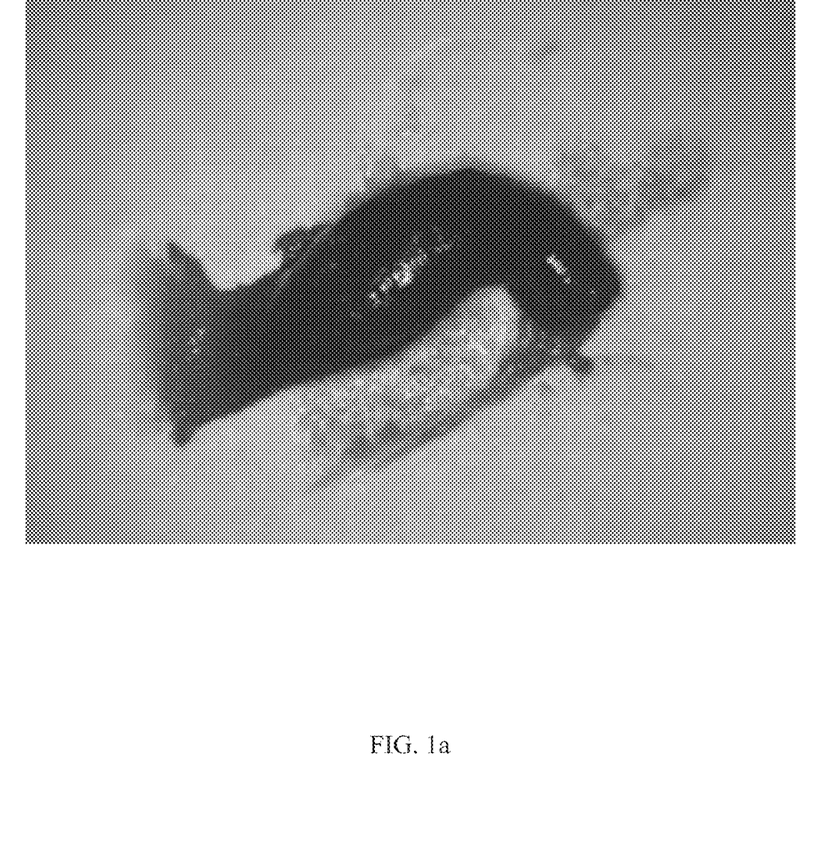
FIG. 1a shows a photograph of the resulting product after extraction and purification of a first sample following the protocol of Example 1.
Figure 1B:
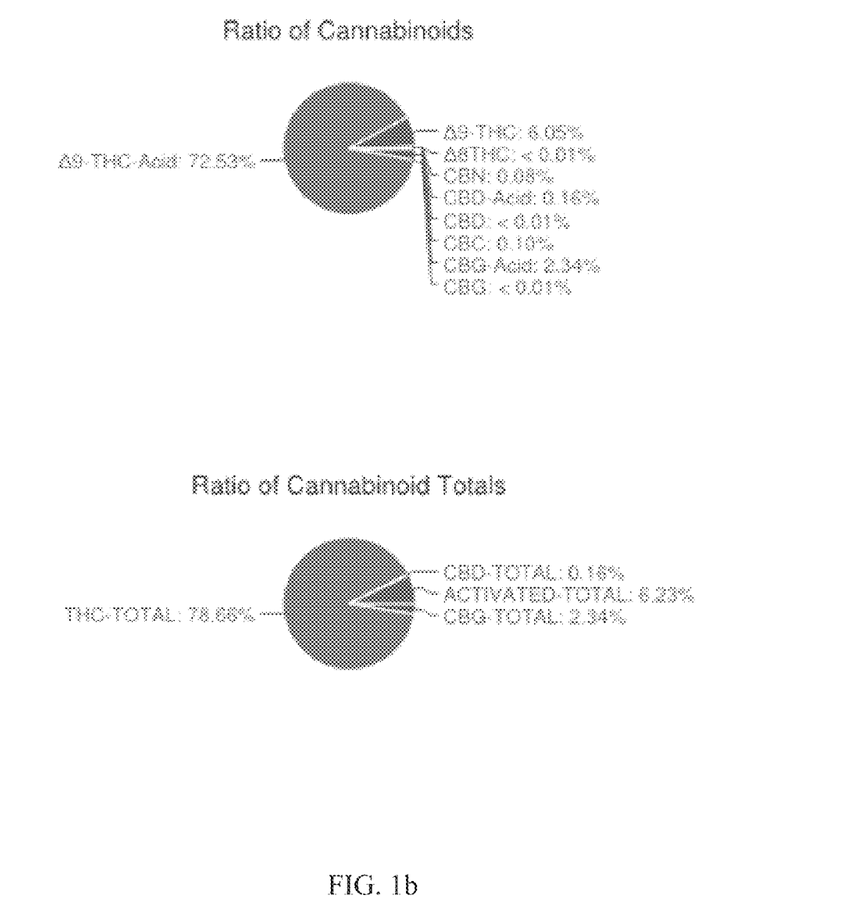
FIG. 1b shows pie charts of the cannabinoid and terpene compositions of the first sample.
Figure 1C:
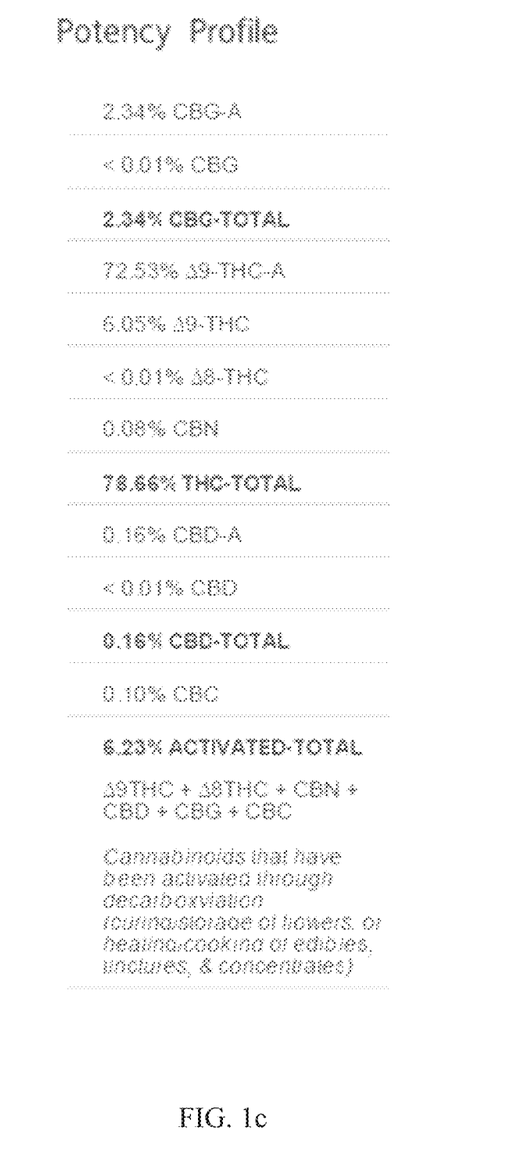
FIG. 1c shows a table of the cannabinoid composition of the first sample.
Figure 1D:
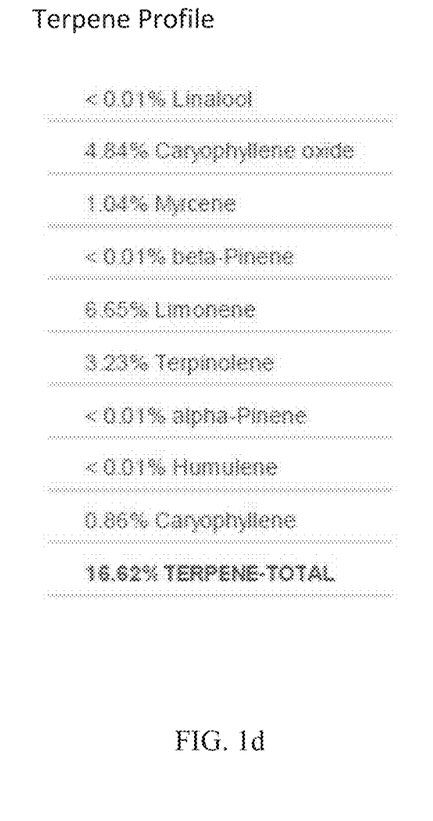
FIG. 1d shows a table of the terpene composition of the first sample.

Once an appropriate amount of solvent was been recovered, the apparatus was removed from the heat source, disassembled, and the contents of the RBF poured into a shallow dish. The residual solvent was removed by evaporation and vacuum purging. Analysis of the resulting purified cannabis extract is shown in FIGS. 1b through 1d.

Example 2—Extraction Protocol Example

One pound of crude cannabis solids (e.g., flower, sugar trim, and/or trim) was separated to break the plant matter apart into course chunks A 6 L APOTHECARIAN apparatus was equipped with a condenser through which ice cold water was circulated. The apparatus was charged with 500 mL ethyl acetate (EtOAc) and approximately 3 oz. of crude cannabis solids were loaded at a time. The temperature was raised to reflux, and once the solvent began to drip through the plant matter the time was noted. After approximately 5 minutes, the condenser was removed from the heat source and allowed to cool. The spent plant material was removed and a fresh batch loaded. More solvent was loaded as well.

Figure 2A:
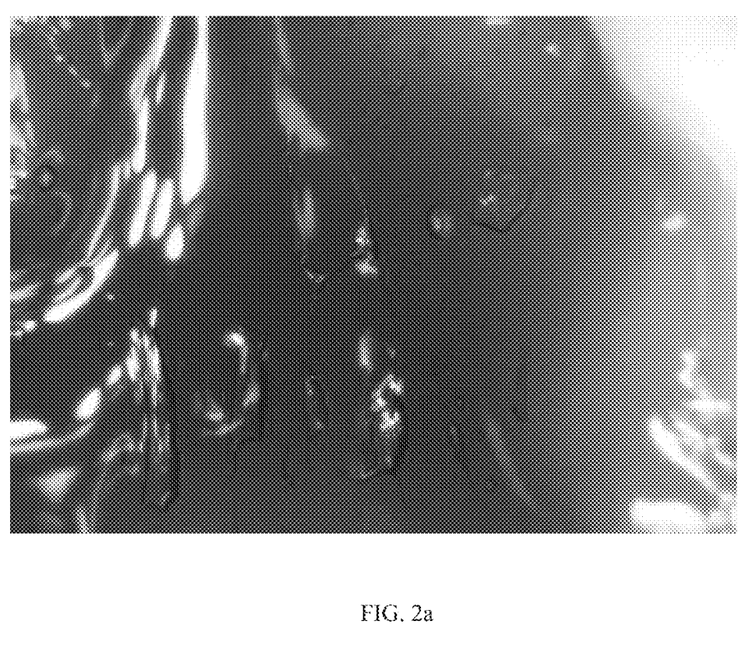
FIG. 2a shows a photograph of the resulting product after extraction and purification of a second sample following the protocol of Example 2.
Figure 2B:
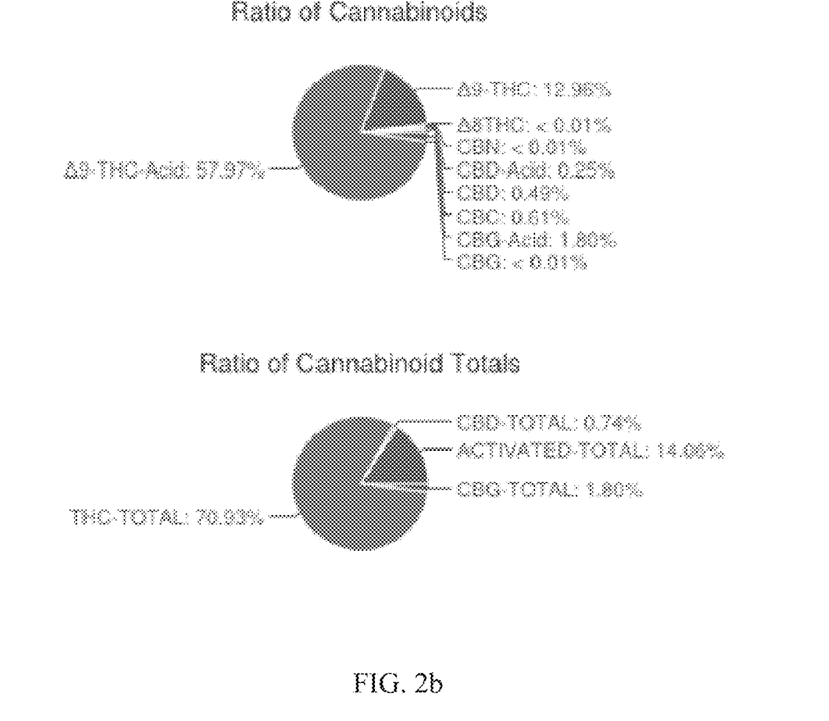
FIG. 2b shows pie charts of the cannabinoid and terpene compositions of the second sample.
Figure 2C:
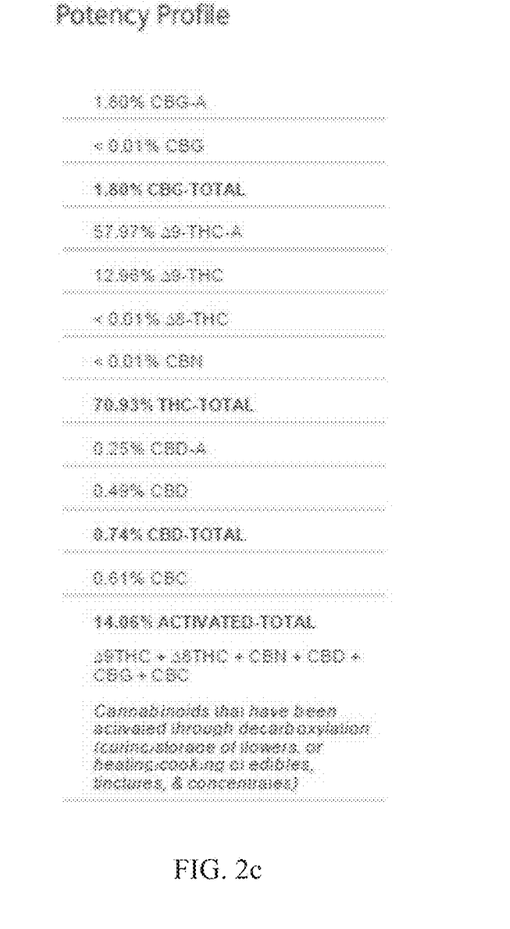
FIG. 2c shows a table of the cannabinoid composition of the second sample.
Figure 2D:
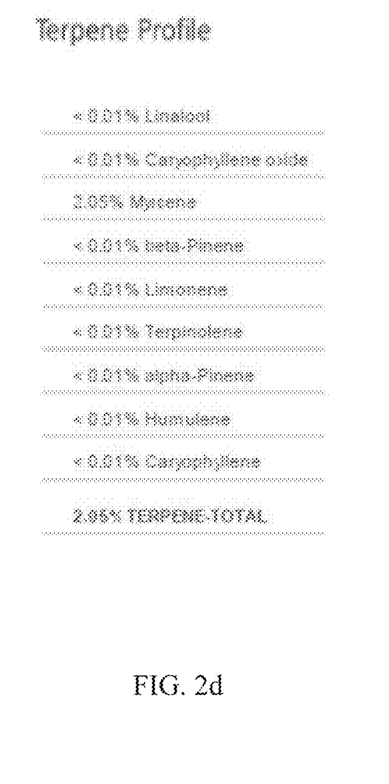
FIG. 2d shows a table of the terpene composition of the second sample.

Once all of the plant matter was extracted, the solvent with cannabis extract was cooled to room temperature, transferred to a beaker, treated with anhydrous food grade sodium sulfate, treated with food grade activated charcoal, and filtered. The solvent was then recovered by simple distillation. The final product was purged and a sample sent for analytical testing. Results: 70% THC and 2% terpenes. The remainder is assumed to be waxes. The waxes can be removed either by traditional alcoholic winterization, winterization in situ (in in the EtOAc, after treatment and filtering), or by optimizing the extraction parameters to selectively remove the cannabinoids and terpenes while leaving the waxes behind. Analysis of the resulting purified cannabis extract is shown in FIGS. 2b through 2d.

Example 3

4.5 pounds of Cannabis sativa trim was ground in a food processor. The material was loaded into a grain steeping bag, and placed into the extraction chamber. Approximately 10 L of ethyl acetate was added (until the plant material was completely covered with solvent). This was allowed to soak for 30 minutes before the grain steeping back was removed from the solvent, and suspended in the extraction chamber and allowed to drain.

A Buchner funnel was prepared with a Whatman #1 filter and a large coffee filter. About 1 pound of sodium sulfate was added in a layer to the coffee filter, followed by about a pound of activated carbon in a layer on top of the sodium sulfate. The extraction mixture was filtered through this, changing its appearance from green to yellow/brown.

The resulting purified extraction mixture was distilled with heat (78° C.), resulting in a completely decarboxylated resin. The overall yield was 10.5%. The resin was analyzed, the results of which are shown in Table 1 below:

TABLE 1

| Compound: | Percent of Resin: |
| --- | --- |
| $\Delta^9$-THC | 74.28% |
| $\Delta^9$-THC-A | <0.01% |
| CBG | 2.34% |
| CBN | 0.44% |
| CBD | 0.37% |
| Total Terpenes | 9.72 |

Example 4

1.5 pounds of Cannabis sativa trim was loaded into a grain steeping back (without grinding the plant material) and placed into the extraction chamber. Approximately 5 L of ethyl acetate was added (until the plant material was completely covered with solvent). This was allowed to soak for 15 minutes before the grain steeping back was removed from the solvent, and suspended in the extraction chamber and allowed to drain.

A Buchner funnel was prepared with a Whatman #1 filter and a large coffee filter. About 1 pound of sodium sulfate was added in a layer to the coffee filter, followed by about a pound of activated carbon in a layer on top of the sodium sulfate. The extraction mixture was filtered through this.

The resulting purified extraction mixture was loaded into a 6 L capacity rotary evaporator and vacuum distilled under the following conditions: Full vacuum, −20° C. chiller, 25° C. water bath, and 75 rpm rotation of the rotating flask.

Example 5

Figure 3:
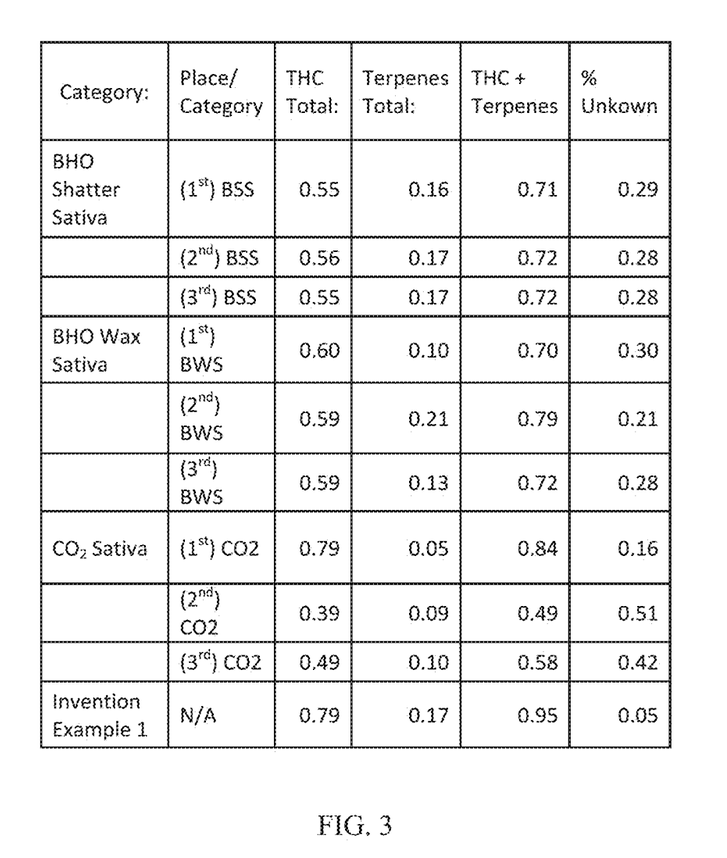
FIG. 3 shows the result of performing the extraction on ten different samples of cannabis in both tabular and bar graph form.

The chart shown in FIG. 3 compares the analytical results of the method of Example 1 above to the award winners from the 2014 Concentrates Cup. It can be seen from the chart that the method of example 1 produces results that are on par with, if not superior to, the best possible results from currently used methods.

The disclosure above encompasses multiple distinct inventions with independent utility. While each of these inventions has been disclosed in a particular form, the specific embodiments disclosed and illustrated above are not to be considered in a limiting sense as numerous variations are possible. The subject matter of the inventions includes all novel and non-obvious combinations and subcombinations of the various elements, features, functions and/or properties disclosed above and inherent to those skilled in the art pertaining to such inventions. Where the disclosure or subsequently filed claims recite "a" element, "a first" element, or any such equivalent term, the disclosure or claims should be understood to incorporate one or more such elements, neither requiring nor excluding two or more such elements.

Applicant(s) reserves the right to submit claims directed to combinations and subcombinations of the disclosed inventions that are believed to be novel and non-obvious. Inventions embodied in other combinations and subcombinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

The invention claimed is:

1. A method of purifying *cannabis* consisting essentially of:
   (a) extracting crude *cannabis* with ethyl acetate to yield a *cannabis* extract;
   (b) dewatering the *cannabis* extract, consisting essentially of contacting the *cannabis* extract with a solid dewatering agent selected from the group consisting of sodium sulfate, magnesium sulfate and silica;
   (c) filtering the extract from the solid dewatering agent to yield a dewatered extract;
   (d) distilling the dewatered extract to remove a majority of the ethyl acetate, thereby creating the purified *Cannabis* extract.

* * * * *